US007220383B2

United States Patent
Anderson et al.

(10) Patent No.: US 7,220,383 B2
(45) Date of Patent: May 22, 2007

(54) METHOD AND INSTRUMENT FOR AUTOMATED ANALYSIS OF FLUID-BASED PROCESSING SYSTEMS

(75) Inventors: Marc R. Anderson, Santa Clara, CA (US); Larry N. Stewart, San Jose, CA (US); Howard M. Kingston, Pittsburgh, PA (US)

(73) Assignee: Metara, Inc., Sunnyvale, CA (US)

( * ) Notice: Subject to any disclaimer, the term of this patent is extended or adjusted under 35 U.S.C. 154(b) by 0 days.

(21) Appl. No.: 10/086,025

(22) Filed: Feb. 28, 2002

(65) Prior Publication Data

US 2003/0013199 A1    Jan. 16, 2003

Related U.S. Application Data

(60) Provisional application No. 60/305,437, filed on Jul. 13, 2001.

(51) Int. Cl.
| | |
|---|---|
| *G01N 33/20* | (2006.01) |
| *G01N 30/72* | (2006.01) |
| *B01D 59/44* | (2006.01) |
| *H01J 49/26* | (2006.01) |

(52) U.S. Cl. .................. 422/62; 250/281; 250/282; 250/287; 422/68.1; 422/81; 436/43; 436/50; 436/56; 436/73; 436/79; 436/80; 436/81; 436/82; 436/83; 436/84; 436/173; 436/174; 436/179; 436/181; 436/182

(58) Field of Classification Search ............... 436/43, 436/50, 52–53, 56, 73, 79–84, 173–174, 436/179, 181–182; 422/62, 68.1, 81; 250/281–282, 250/287

See application file for complete search history.

(56) References Cited

U.S. PATENT DOCUMENTS 4,132,605 A    1/1979 Tench et al.

(Continued)

FOREIGN PATENT DOCUMENTS

GB    2273561    *  6/1994

(Continued)

OTHER PUBLICATIONS

Marchante-Gayon, J. M. et al, Special Publication—Royal Society of Chemistry 1997, 202, 85-94.*

(Continued)

*Primary Examiner*—Arlen Soderquist
(74) *Attorney, Agent, or Firm*—Jonathan W. Hallman; MacPherson Kwok Chen & Heid LLP (57) ABSTRACT

An analytical apparatus to monitor fluid systems has at least one extraction module having a raw-sample reservoir connected by input fluid conduit to individual ones of said fluid systems, to extract raw samples for analysis from said fluid systems, one or more modification modules comprising additive materials to modify the extracted raw samples prior to analysis, an analytical device to receive at least a portion of said raw samples in an ordered sequence, and to determine concentration of at least one constituent of said sample portion, fluid-handling apparatus for transferring fluid through the analytical apparatus, and a computerized control and management system to manage operations of component modules and devices, and to report analytical results. The apparatus is characterized in that the control and management system coordinates extraction of raw samples, modification as needed, introduction of fluids to the analytical device, and reporting of analytical results on a continuous basis over plural cycles.

3 Claims, 7 Drawing Sheets

U.S. PATENT DOCUMENTS

| | | | |
|---|---|---|---|
| 4,324,621 A | 4/1982 | Kerby | |
| 4,479,852 A | 10/1984 | Bindra et al. | |
| 4,713,772 A * | 12/1987 | Carlson | 702/30 |
| 4,917,777 A | 4/1990 | Fisher | |
| 4,975,328 A | 12/1990 | Hirose et al. | |
| 5,012,052 A | 4/1991 | Hayes | |
| 5,054,309 A * | 10/1991 | Mettes et al. | 73/1.03 |
| 5,182,131 A | 1/1993 | Hashimoto et al. | |
| 5,192,403 A | 3/1993 | Chang et al. | |
| 5,235,186 A * | 8/1993 | Robins | 250/288 |
| 5,414,259 A | 5/1995 | Kingston | |
| 5,572,024 A | 11/1996 | Gray et al. | |
| 5,696,378 A | 12/1997 | Busch et al. | |
| 5,703,360 A | 12/1997 | Fischer et al. | |
| 5,777,214 A * | 7/1998 | Thompson et al. | 73/61.59 |
| 5,872,357 A | 2/1999 | Flanagan | |
| 5,892,458 A * | 4/1999 | Anderer et al. | 340/10.41 |
| 5,983,734 A * | 11/1999 | Mathur et al. | 73/864.24 |
| 6,032,513 A | 3/2000 | Chorush et al. | |
| 6,280,602 B1 | 8/2001 | Robertson | |
| 6,730,517 B1 * | 5/2004 | Koster et al. | 436/47 |

FOREIGN PATENT DOCUMENTS

| | | | |
|---|---|---|---|
| GB | 2294761 | * | 5/1996 |
| JP | 61-13153 | * | 1/1986 |
| JP | 11-6788 | * | 1/1999 |
| JP | 131310 | * | 5/2000 |
| WO | 99/39198 | * | 8/1999 |
| WO | 99/48602 | * | 9/1999 |

OTHER PUBLICATIONS

Wiederin, D. R. et al, Analytical Chemistyr 1991, 63, 1626-1631.*
Seubert, A. Fresenius J. Anal. Chem. 1999, 364, 404-409.*
Dahmen, J. et al, Fresenius J. Anal. Chem. 1997, 359, 410-413.*
Beauchemin, D. et al, Analytical Chemistry 1997, 69, 3183-3187.*
Bartels, H. et al, GIT Fachz. Lab. 1977, 21, 1276-1278 and 1280-1282.*
Slobodnik J. et al, Journal of Chromatography A 1996, 730, 353-371.*
Huang, C.-C. et al, Analytical Chemistry 1997, 69, 3930-3939.*
Multala, R. et al, Kemia-Kemi 1977, 4, 627-631.*
Stieg, S. et al, Analytical Chemistry 1980, 52, 796-800.*
Israel, Y. et al, Analyst, 1989, 114, 1259-1265.*
Lasztity, A. et al, Journal of Analytical Atomic Spectrometry 1989, 4, 761-766.*
Maxwell, S. L., III et al, Chemical Abstracts, 1990, 115, abstract 125715.*
Klinkenberg, H. et al, Spectrochimica Acta, 1993, 48B, 649-661.*
Goossens, J. et al, Analytica Chimica Acta 1994, 293, 171-181.*
Heumann, K. G. et al, Journal of Analytical Atomic Spectrometry 1994, 9, 1351-1355.*
Hegy, G. et al, Chemical Abstracts 1996, 126, abstract 220107.*
Albertus, F. et al, Analyst, 1999, 124, 1373-1381.*
Dobney, A. et al, Analytica Chimica Acta 2000, 420, 89-94.*
Maxwell, S. L., III et al, Nuclear Materials Management 1990, 19, 199-202.*
Dohi, K. et al, R&D, Research and Development (Kobe Steel Ltd.) 1991, 41, 146-147.*
Agudo, M. et al, Analytica Chimica Acta 1992, 264, 265-273.*
Park, C. J. et al, Analytical Science & Technology 1995, 8, 427-434.*
Waygood, J. B., Proceedings of the Chemists' Conference 1995, 47th, 64-68.*
Ketterer, M. E. et al, Analytical Chemistry 1996, 68, 883-887.*
Jinghong, H. et al, Sensors and Actuators B 1996, 35-36, 422-426.*
Stewart, I. I. et al, Journal of Analytical Atomic Spectrometry 1996, 11, 1203-1214.*
Olesik, J. W. et al, Journal of Analytical Atomic Spectrometry 1997, 12, 507-515.*
Zoorob, G. et al, Journal of Analytical Atomic Spectrometry 1997, 12, 517-524.*
Baron, D. et al, Journal of Environmental Quality 1998, 27, 844-850.*
Raffaelli, A. et al, Inorganica Chimica Acta 1998, 275-276, 462-469.*
May, T. W. et al, Atomic Spectroscopy 1998, 19, 143-149.*
Ross, A. R. S. et al, Analytical Chemistry 1998, 70, 2225-2235.*
Schramel, O. et al, ournal of Chromatography, A 1998, 819, 231-242.*
Godec, R. et al, Semiconductor Pure Water and Chemicals Conference 1999, 18th, 91-110.*
Szpunar, J. et al, Chemia Analityczna (Warsaw) 1999, 44, 351-362.*
Henderson, W. et al, Inorganica Chimica Acta 1999, 294, 183-192.*
Mollah, S. et al, Analytical Chemistry 2000, 72, 985-991.*
Whistler, W. J. et al, International Journal of Mass Spectrometry and Ion Physics 1983, 46, 159-162.*
Shushan, B. et al, ACS Symposium Series 1986, 295, 284-293.*
Renn, C. N. et al, Analytical Chemistry 1989, 61, 1915-1921.*
Lindberg, C. et al, Journal of Chromatography 1991, 554, 215-226.*
Lindberg, C. et al, Biological Mass Spectrometry 1992, 21, 525-533.*
Grundig, B. et al, Journal of Biotechnology 1993, 31, 277-287.*
Champion, B. R., Publications of the Australasian Institute of Mining and Metallurgy 1993, Jul. 1993, 257-265.*
Welz, B. et al, Pure and Applied Chemistry 1993, 65, 2465-2472.*
Lee, M.-K. et al, Journal of the Chinese Chemical Society 1994, 41, 711-717.*
Einarsson, O. et al, Journal of Automatic Chemistry 1995, 17, 21-24.*
Agudo, M. et al, Analytica Chimica Acta 1995, 308, 77-84.*
Frary, B. D., Analyst 1998, 123), 233-237.*
Zerihun, A. et al, LC-GC 1999, 17, 862, 864.*
Fassett et al., *Determination of Nanogram Quantities of Vanadium in Biological Material by Isotope Dilution Thermal Ionization Mass Spectrometry with Ion Counting Detection*, Anal. Chem. (Nov. 1985), pp. 2474-2478, V57, No. 13.
Fassett et al., *Isotope Dilution Mass Spectrometry for Accurate Elemental Analysis*, Anal. Chem. (May 15, 1989), pp. 643A-649A V61, No. 10.
Viczian et al., *On-line Isotope Dilution and Sample Dilution by Flow Injection and Inductively Coupled Plasma Mass Spectrometry*, J. Anal. Atom. Spectro. (Apr. 1990), pp. 125-133, V5.
Rottmann et al., *Determination of Heavy Metal Interactions with Dissolved Organic Materials in Natural Aquatic Systems by Coupling a High-Performance Liquid Chromatography System with an Inductively Coupled Plasma Mass Spectrometer*, Anal. Chem. (Nov. 1, 1994), pp. 3709-3715, V66.
Heumann et al., *Elemental Speciation with Liquid Chromatography-Inductively Coupled Plasma Isotope Dilution Mass Spectrometry*, J. Anal. Atom. Spectro. (Dec. 1994), pp. 1351-1355 V9.
Horn et al., *Comparison of heavy metal analyses in hydrofluoric acid used in microelectronic industry by ICP-MS and thermal ionization isotope dilution masss spectrometry*, Fresenius J. Anal. Chem (1994), pp. 286-292, V350.
Rottman et al., *Development of an on-line isotope dilution technique with HPLC/ICP-MS for the accurate determination of elemental species*, Fresenius J. Anal Chem. (1994), pp. 221-227, V350.
Cole, *Electrospray Ionization Mass Spectrometry: Fundamentals, Instrumentation and Applications*, John Wiley & Sons, Inc. (1997), New York.
Stewart, *Electrospray mass spectrometry: a tool for elemental speciation, Spectrochimica*, Acta. (1999), pp. 1649-1695, Part-B, vol. 54.
*International Technology Roadmap for Semiconductors 1999 Edition: Defect Reduction*, Sematech, Austin, TX, pp. 269-293.
Newton et al., *Analysis of Copper Plating Baths—Suppressors and Levelers*, Electrochemical Society Proceedings, pp. 1-5, V2000-27.

* cited by examiner

METHOD AND INSTRUMENT FOR AUTOMATED ANALYSIS OF FLUID-BASED PROCESSING SYSTEMS

CROSS REFERENCE TO RELATED APPLICATION

This application claims the benefit of U.S. Provisional application Ser. No. 60/305,437, filed Jul. 13, 2001.

CROSS-REFERENCE TO RELATED DOCUMENTS

The present application is related to an issued U.S. Pat. No. 5,414,259, issued to Howard M. Kingston on May 9, 1995, incorporated herein in its entirety by reference, to a co-pending patent application Ser. No. 09/015,469, filed Jan. 29, 1998, also incorporated in its entirety by reference, and to a provisional patent application filed Jan. 29, 2001, bearing Ser. No. 60/264,748, now U.S. Ser. No. 10/004,627 filed Dec. 4, 2001, which is also incorporated herein in its entirety by reference.

FIELD OF THE INVENTION

The present invention is in the area of chemical analysis of fluid systems, such as wet baths used in processing, and pertains more particularly to instrumentation for sampling such systems, processing such samples for analysis, and presenting the processed samples to analytical equipment for measurement, in an automated fashion unattended for extended time periods.

BACKGROUND OF THE INVENTION

This invention relates specifically to instrumentation enabling methods for in-process, automated, continuous analysis of fluid systems for such as contamination, specified concentration of specific species, and the like. In the present application analysis of liquid baths containing processing solutions used in front-end processing in semiconductor manufacturing is used as a specific example, but the uses of the instrument are not limited to this exemplary application. The method and apparatus of the present invention are applicable in many areas, such as environmental, medical, pharmaceutical, industrial processing and other related and unrelated fields.

In a preferred embodiment the system of the invention uses a modified form of Isotope Dilution Mass Spectrometry (IDMS), known to the inventors as Speciated Isotope Dilution Mass Spectrometry (SIDMS). The exemplary method is an elemental and speciation threshold measurement method that is optimized for quality assurance at and near instrumental detection limits. The threshold measurement method is automated for unattended operation, and describes an In-process, Atmospheric Pressure Ionizer, Mass Spectrometer (IP-API-MS). The IP-API-MS apparatus is designed for identification and quantification of elemental contaminants or compounds and species in fluids, and in the exemplary case, liquid solutions.

Mass Spectrometry instrumentation is frequently used as the technique of choice in measuring parts-per-billion (ppb) and sub-ppb levels of elements and compounds in aqueous and other solutions of other solvents and reagents, as well as in gases. However, mass spectrometers typically must be operated and regularly calibrated by experienced technicians. There are, however, a wide variety of applications wherein continuous and unattended operation of the Mass Spectrometer would be highly desirable. These cases include remote operation, around the clock monitoring, and operation either in hostile environments, or where human interaction must be minimized, among others.

One good example of an application wherein around-the-clock, unattended monitoring is highly desirable is that of contamination-monitoring and control for wet-bath processing in manufacturing in the semiconductor industry. There are a variety of processes in semiconductor manufacturing wherein wafers in process must be immersed and treated in various ways, such as cleaning, neutralizing, etching and the like.

In the example of semiconductor manufacturing, various types of contamination are a critical issue; in particular contamination by particulate matter, as even very tiny particles may be larger than device and connection geometry in various stages of manufacture. At least partly for this reason a rigid clean-room environment is absolutely necessary, and minimal human interaction is highly desirable. Because of this, development and implementation of real time, in-situ sensors into clean room processes is considered by many to be one of the top five defect reduction challenges in the future of the industry. For further information regarding defect reduction in this industry, the article from International Technology Roadmap for Semiconductors 1999 Edition: *Defect Reduction*, Sematech, Austin Tex., 1999, (pg. 270), is incorporated herein by reference. There are many other references supporting this need, which is notoriously well-known in the art.

In order to accomplish unattended operation for wet bath contamination and constituent monitoring, apparatus must be developed that will automatically monitor constituent concentrations at their threshold level, accurately and without the need to compensate for inevitable systematic errors associated with instrument drift. Quantitation of concentration may then be obtained without the need for traditional calibration once the threshold level has been exceeded.

Figure 1:
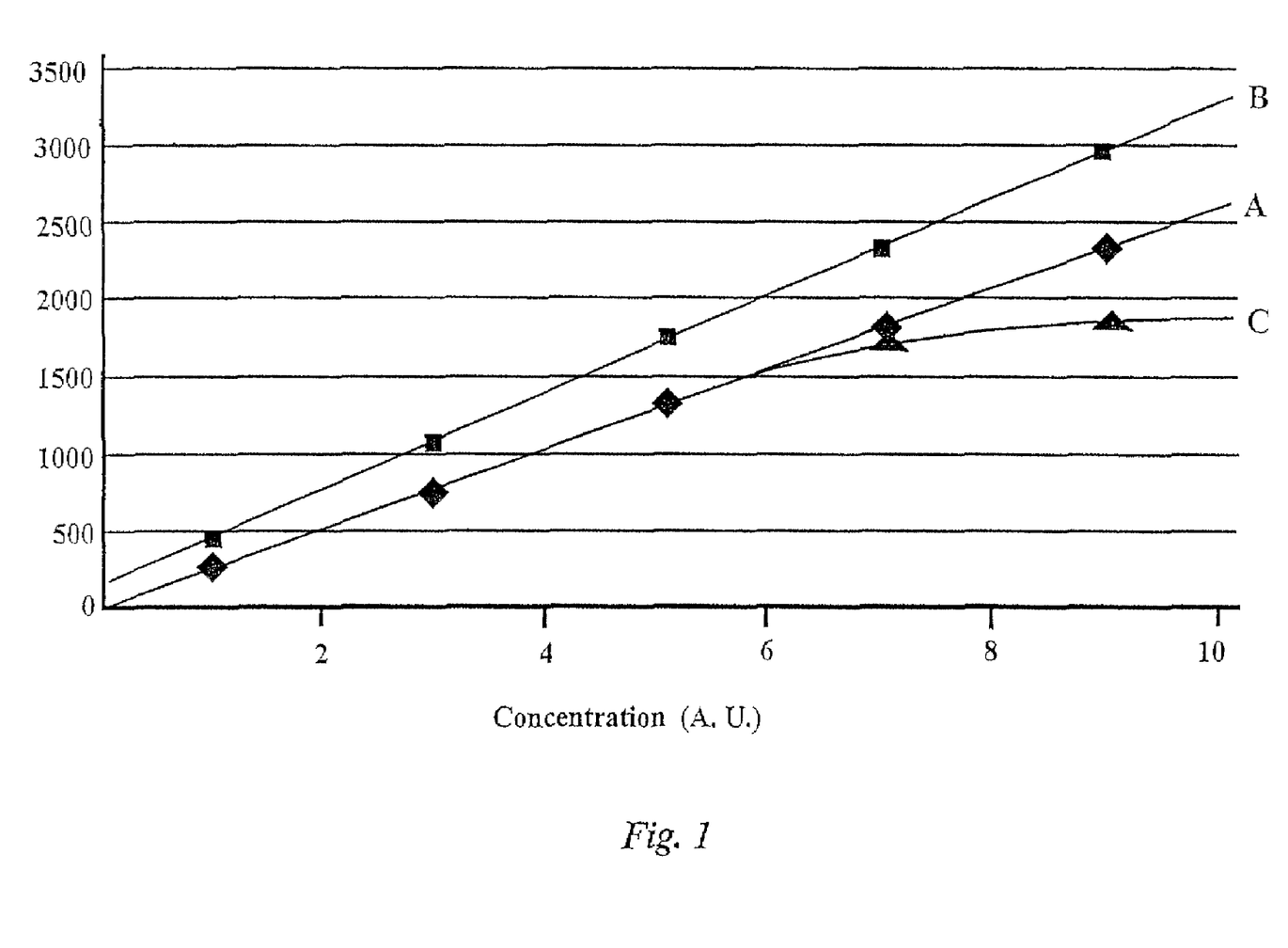
FIG. 1 is an exemplary graph showing calibration curves for a mass spectrometry instrument, and how the curves may change under various circumstances.

Prior art calibration techniques typically use calibration standards to generate a calibration curve relating instrument response to concentration of standards. Such a calibration curve is used to determine the concentration of unknown samples. A typical calibration curve of this sort is illustrated as FIG. 1 in this specification (curve A). Prior art techniques do not yield accurate results if the instrument response drifts or there is a response shift caused by a difference in the matrices between a standard and a sample. Mass spectrometers, typically used in such measurements, are especially susceptible to rapid drift, causing a change in the calibration response as shown in FIG. 1 (curve B). Such rapid drift results in a need for frequent calibrations that are normally performed by experienced technicians.

In calibration procedures, a considerable effort must be made to match the matrices of the sample and standard, to ensure ionization efficiencies, ionization suppression, or enhancements remain constant between a sample and the standard. Viscosity differences between the sample and the standard matrices may also cause unequal instrument responses associated, for example, with changing sample introduction rates, and are inevitable in real-world situations. Matrix effects altering solution viscosity or ionization efficiency can result in calibration changes such as shown in FIG. 1 (curve C). Clearly, in order to achieve full-time, real-time, measurement without human intervention for calibration of maintenance, a method and apparatus must be provided that overcomes these prior-art requirements.

The present inventors have chosen an enhancement of a known technique for achieving calibration-free mass spectrometry measurements. The known technique is Isotope Dilution Mass Spectrometry, hereinafter IDMS. In IDMS, one takes advantage of well-known, naturally-occurring isotope ratios in essentially all elements. For example; it is well-known that the average atomic mass of copper (Cu) in the natural state is 63.546, consisting of isotopes 62.9396 at 69.2% and 64.9276 at 30.8%. Very generally speaking, assuming an analysis for Cu content is required, one takes a sample of the solution to be analyzed, spikes the sample with an enriched standard solution having a substantially different isotope ratio than the naturally-occurring ratio, introduces the spiked sample to a mass spectrometer, and records the measured mass ratio between the isotopes. The measurement is going to differ from the naturally-occurring ratio and the standard spike ratio, and from the measured ratio, knowing the quantity of the original sample, and the quantity of the spike solution, one can calculate the single unknown, that being the concentration of Cu in the original sample.

IDMS, in a form known as Speciated Isotope Dilution Mass Spectrometry, hereinafter SIDMS, is a patented technique, described in enabling detail in U.S. Pat. No. 5,414,259, issued May 9, 1995 to inventor Howard M. Kingston Ph.D, and incorporated herein in its entirety by reference. The teaching in the referenced patent describes both the general (previously known) and the special (patented) technique as adapted for the instrument in embodiments of the present invention.

There are a considerable number of other available references describing IDMS, among them:

Fassett, J. D., Paulsen, P. J. *Isotope-dilution mass spectrometry for accurate elemental analysis, Anal. Chem.* (1989) 61 643A–649A.

Rottmann, L., Heumann, K. G., *Development of an on-line Isotope Dilution Technique with HPLC/ICP-MS for the accurate determination of elemental species. Fresenius J. Anal. Chem.*, (1994) 350 221–227.

Heumann, K. G., Rottmann, L., Vogl, J., *Elemental Speciation with Liquid Chromatography-Inductively Coupled Plasma Isotope Dilution Mass Spectrometry. J. Anal. Atom. Spectro.* (1994) 9 1351–1355.

Fassett, J. D. and Kingston, H. M., *Determination of Nanogram Quantities of Vanadium in Biological Material by Isotope Dilution Thermal Ionization Mass Spectrometry With Ion Counting Detection, Anal. Chem.*, (1985) 57 2474–2478, all of which are incorporated herein in their entirety by reference.

It will be apparent to the skilled artisan that employing the patented techniques of the above-referenced patent to Kingston is an excellent first step in accomplishing full-time, real-time mass spectrometry analysis of fluid systems, but that there are many other challenges in sample collection, sample handling, sample spiking, dilution, control, and many other areas to accomplish such a robust measurement and control system in real applications, such as in wet-bat analysis in semiconductor manufacturing, which has been selected as an exemplary application for describing the apparatus and methods of the present invention.

What is clearly needed is a modular system for deployment in real-world applications, which provides for all of the logistics of sample collection, flow-rate manipulation with extreme accuracy, sample alteration and preparation, extremely accurate spiking, sample introduction to analytical systems (mass spectrometry), information gathering and communication, on-line cleaning and purging between sample collection, and overall control among other things; and it is to apparatus and methods for accomplishing these ends reliably and efficiently that the following enabling descriptions of such a system is devoted.

SUMMARY OF THE INVENTION

In accordance with the invention, an apparatus for in-process ratio mass spectrometry is provided. The apparatus includes: a spike dilution apparatus configurable to dilute a spike having a first concentration to produce a processed spike having a diluted second concentration; a mixer configured to mix the processed spike and an extracted sample having at least one analyte to permit equilibration therebetween; an atmospheric pressure ionizer (API) configured to ionize the equilibrated extracted sample and processed spike to produce ions; a mass spectrometer configured to process the ions by ratio determination; and a control system adapted to automatically control the spike dilution apparatus, the mixer, the API, and the mass spectrometer such the sample is mixed with the processed spike, ionized, and processed by the mass spectrometer, the control system being further configured to use the ratio measured by the mass spectrometer to characterize the concentration of the at least one analyte in the extracted sample.

In accordance with another aspect of the invention, a method of automatically analyzing an analyte is provided. The method includes the acts of: diluting a spike having a first concentration to produce a processed spike having a second concentration; wherein the second concentration is selected based upon an estimate of a concentration of the analyte in a sample; mixing the processed spike and the sample to produce an equilibrated mixture of the processed spike and sample; ionizing the equilibrated mixer using an atmospheric-pressure-ionizer to produce ions; processing the ions in a mass spectrometer to produce a response ratio; and characterizing the concentration of the at least one analyte using the response ratio.

In embodiments of the present invention, taught in enabling detail below, for the first time a sampling system is provided wherein samples from fluid baths may be drawn, and concentrations analyzed and reported, on a continuous and fully automated basis.

It is an object of the present invention to provide an analytical apparatus and an associated method to monitor fluid systems by extracting raw samples and modifying the same chemically and/or as to concentration with subsequent analytical analysis being performed with the assistance of automated computerized control.

It is a further object of the present invention to provide such a system that employs isotopic ratios in effecting such determinations on liquid samples.

It is another object of the present invention to provide such a system that has unique liquid handling subsystems, which provide for automated continuous processing.

It is another object of the present invention to provide such systems that facilitate decision control over raw sample amounts, as well as chemical modifications and dilutions thereto.

It is another object of the present invention to provide such a system that is adapted for online or adjacent analysis with respect to industrial process wet-baths.

These and other objects of the invention would be more fully understood from the following detailed description of the invention on reference to the illustrations appended hereto.

DESCRIPTION OF THE PREFERRED EMBODIMENTS

Overview

Speciated Isotope Dilution Mass Spectrometry (SIDMS), as described in the '259 patent to Kingston referenced above, has been developed to assess the quantification of species and also their transformations. In SIDMS a predetermined species is specifically isotopically labeled and introduced to accomplish such measurements. The species of interest is previously known and specifically evaluated. In this invention the labeled species (frequently multiple species simultaneously) are being created in solution and are not previously determined in composition and structure until evaluated for structural information. Quantification is of the elemental ion and speciation information first established in-process through dynamic equilibrium established with a non-complexing salt of an enriched stable isotope in real time and in-process.

In the SIDMS method, as enabled in embodiments of the present invention, one may accomplish unattended operation of an apparatus that will accurately monitor elemental concentration threshold levels, identify, and quantify elemental contaminants or compounds and species in fluids. Unlike traditional IDMS this method enhances and improves measurement at and near the detection limit of mass spectrometers.

Generally, the apparatus in embodiments of the present invention uses the SIDMS method for In-process measurement, using an Atmospheric Pressure Ionizer coupled to a Mass Spectrometer (IP-API-MS). The IF-API-MS apparatus is designed for identification and quantification of elemental contaminants or compounds and species in fluids without reliance upon a high temperature argon plasma for equilibrium or requiring a high-pressure liquid chromatography HPLC separation step prior to measurement.

The instrument in its several embodiments described in enabling detail below, and others within the spirit and scope of the invention, integrates application flexibility and growth along with key attributes that must be incorporated to meet these needs. The instrument has multiple configurations. These multiple configurations are to deal with gases and liquids. Within the liquid analysis regime, the configurations accommodate ultra pure water (UPW) and a broad assortment of acids and bases that are typically utilized in manufacture of semiconductor devices, used as a particular example in this specification, and also in other industrial applications.

In embodiments to analyze liquids, the instrument utilizes an Electro Spray Time of Flight Mass Spectrometer (ES-TOF-MS) for high-speed measurement in very low parts-per-billion (ppb) range. This ES-TOF-MS is enabled with corrosive-resistant hardware where the application warrants. A second configuration consists of a combination liquid chromatography (LC) pumping system and an Electro Spray Time of Flight Mass Spectrometer (LC-ES-TOF-MS) for measurements in the parts-per-trillion (ppt) range. The electro-spray (ES) is the interface between the LC and MS components and is operated in a non-classical manner.

The instrument in preferred embodiments is computer-controlled, with the flexibility to change operational conditions for various solution compositions, component analytes, and detection limit requirements. Concentration and chemical species quantification are also enabled in this configuration. The instrument in all preferred embodiments is compact, and configured to be located in close proximity to the wet bench or gas related process equipment to be analyzed, and is implemented in materials compatible with a clean room manufacturing environment. Some instruments in current use, such as the inductively-coupled plasma mass spectrometers (ICP-MS), are not compatible with clean room manufacturing environments that are envisioned in this application.

The instrument in preferred embodiments of the present invention is developed to operate unattended for long periods of time, maintaining high degrees of reliability in accuracy and precision. This is accomplished by relying on altered isotopic ratio measurements of elements, which minimizes the use of calibration, and in many cases eliminates it entirely. Additionally, the instrument will measure elements and molecules, along with species of these components, providing data richness required by sophisticated chemistries and evaluation tools.

A clear objective of instruments in preferred embodiments of the present invention is to analyze all the elements in all the solutions used in wafer manufacturing in near real time. In another embodiment the system of the invention has an interface with an interpretive advisory information system that provides process control status and predictions on optimum timing for solution changes and information on whether each solution is within tolerances, based on the specific processes and end.

The analytical tools of the present invention in various embodiments provide near real-time analytical chemical metrology of contaminant concentrations of semiconductor fab reagents and cleaning solutions. These contaminants include, among others, transition metals (e.g., Co, Cr, Cu, Fe, Mn, Ni, Ti, V, and Zn) and complex species of these elements in fab solutions. Generally, however, it is desirable to measure any additional elements present at significant concentrations.

In preferred embodiments measurements are made with 50–500 microliter quantities of solution. The contamination concentration range that must be assessed is mid-ppb to low-ppt. As semiconductor chip geometries continue to shrink, contaminants have even greater effect on the viability of the final products. Additional chemical information will identify key chemical complex ligands and compositions that are responsible for specific chemical reaction events and enable precise optimization of chemical conditions.

Abstract Description of Instrument

Figure 2:
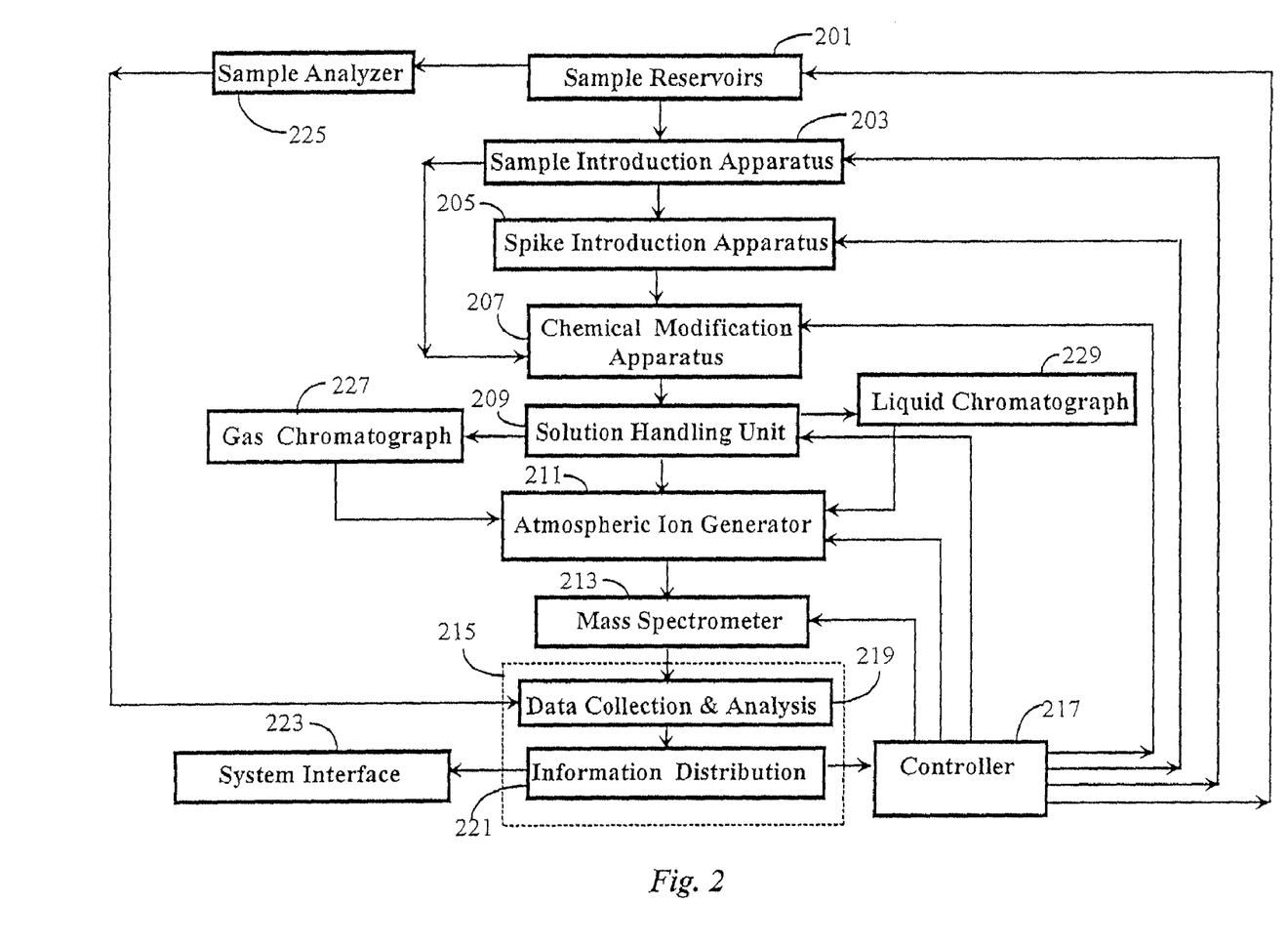
FIG. 2 is a block diagram illustrating, at an abstract level, an exemplary apparatus in an embodiment of the present invention.

FIG. 2 is a block diagram illustrating, at an abstract level, an exemplary apparatus in an embodiment of the present invention, related, where appropriate, to monitoring of wet baths in semiconductor manufacturing as a specific example of application.

In FIG. 2, sample reservoirs 201 represents one or more reservoirs for holding sample solutions prior to pre-processing, spike mixing, and analysis. FIG. 2 is an abstract model, and does not show detail such as apparatus for pulling sample from the processing baths that are monitored, but such apparatus may be assumed to be included, and is described in more detail below. An important function of the sample reservoirs is to provide for an air-gap separation from the wet-bath monitored, and to enable a significant change in flow rate, which is also described in additional detail below.

As described above relative to SIDMS samples may have to be pre-processed in some instances to prepare for analysis. There are a variety of reasons for such pre-treatment, and an equal variety of procedures and chemistry involved. As an example, one of the uses of wet-baths in semiconductor processing is etching oxides and other materials on wafer surfaces. The solutions used in the etching baths may be highly acidic in some cases and highly caustic in others. Some such solutions may be detrimental to elements of the instrument apparatus, and the raw samples have to therefore be treated to substantially neutralize the acid or base nature of the raw sample.

The nature of the instrument in embodiments of the invention is that sample from a sample reservoir is introduced to an equalibrator (equalizer) apparatus, typically a laminar-flow mixing junction to be described more fully below, and, in one instance chemical reagents in solution may be introduced to the same equlibrator. In another instance pre-processed sample is introduced to another equalibrator along with spike solution, and the resulting spiked solution is then introduced to an electrospray system integrated with an atmospheric ion generator for introduction to a mass spectrometer. The overall procedure, at an abstract level, is a sequentially cascaded process ending at injection to the mass spectrometer.

Sample introduction apparatus 203 represents a sub-system for controlled injection of sample from the one or more sample reservoirs 201 into, typically an equalibrator not shown. Spike introduction apparatus 205 represents a sub-system, of which there may be several, for preparing spike solution, that being, as described above, a known mixture of isotopes of the sought-after specie, the ratio differing significantly from the naturally-occurring ratio in the specie in the sample. Chemical modification apparatus 207 represents a subsystem, of which there may also be several in different embodiments of the invention, to serve the number of sample reservoirs and baths being monitored, for injecting in the cascaded process chemicals in precise amounts for pre-treatment of sample before or after spiking, and before analysis.

The order of the introduction and the modification sub-systems shown in FIG. 2 is exemplary only, and can vary considerably, which is why a path from apparatus 203 directly to apparatus 207 is shown, and direct paths are also shown.

Solution handling unit 209 represents sub-systems of fluid conduit, check valves, switching valves, vacuum sub-systems, drive units, and the like for moving samples in precisely-measured increments from one place to the next in the overall instrument.

Once a sample has traversed the cascading system and has been pretreated as necessary and spiked as necessary it is delivered to an atmospheric ion generator 211 which comprises an electrospray sub-system for vaporizing and ionizing the prepared and spiked sample for introduction to a mass spectrometer 213, which may in some embodiments be a quadrapole instrument, and in others a time-of-flight instrument.

It will be appreciated by the skilled artisan that the description thus far has been of a system with potentially a plurality of reservoirs for sample, a plurality of chemical pre-treatment apparatus, and a similar plurality of spiking sub-systems, and that such a system may be dedicated to sequential analysis of a variety of samples, several of which may in various stages of treatment and processing at the same time, with the instrument controlled to sequentially deliver prepared samples to the electrospray, and hence to the mass spectrometer. The mass spectrometer, then, may be generating one spectra after another, providing important information about the concentration of one or more constituents of a plurality of baths connected to the modular system of various embodiments of the present invention.

The instrument described herein in various embodiments is computer-controlled and managed, and various functions of the overall control and data management are provided by a microcroprocessor 215 and controller 217 in FIG. 2. Microprocessor 215 comprises a data collection and analysis system 219 and an information distribution system 221. Mass spectra, among other information, is sent to unit 219, and data may be manipulated in any of a variety of ways, under the auspices of controller 217, executing software proprietary to the system of the invention, and unit 221 delivers processed information to a system (and user) interface 223. In some cases interface 223 provides displayed information for technicians and the like to make decisions involving bath maintenance, and in others, may provide data directly to automated systems enabling bath maintenance. Data and processed information may also be provided to overall fab maintenance software developing historical data to match for many purposes with semiconductor processors resulting subsequently from wafers processed in the monitored baths.

FIG. 2 illustrates a sample analyzer system and path to data collection unit 215, which is an optional apparatus in embodiments of the present invention, and may be used for qualitative analysis of samples, such as pH, temperature, and the like. FIG. 2 also illustrates a gas chromatograph 227 and a liquid chromatograph 229. These units are not needed and not used in many preferred embodiments of the invention, but are useful in some applications, and therefore illustrated at an abstract level herein.

Modular Instrument in a Preferred Embodiment

Figure 3:
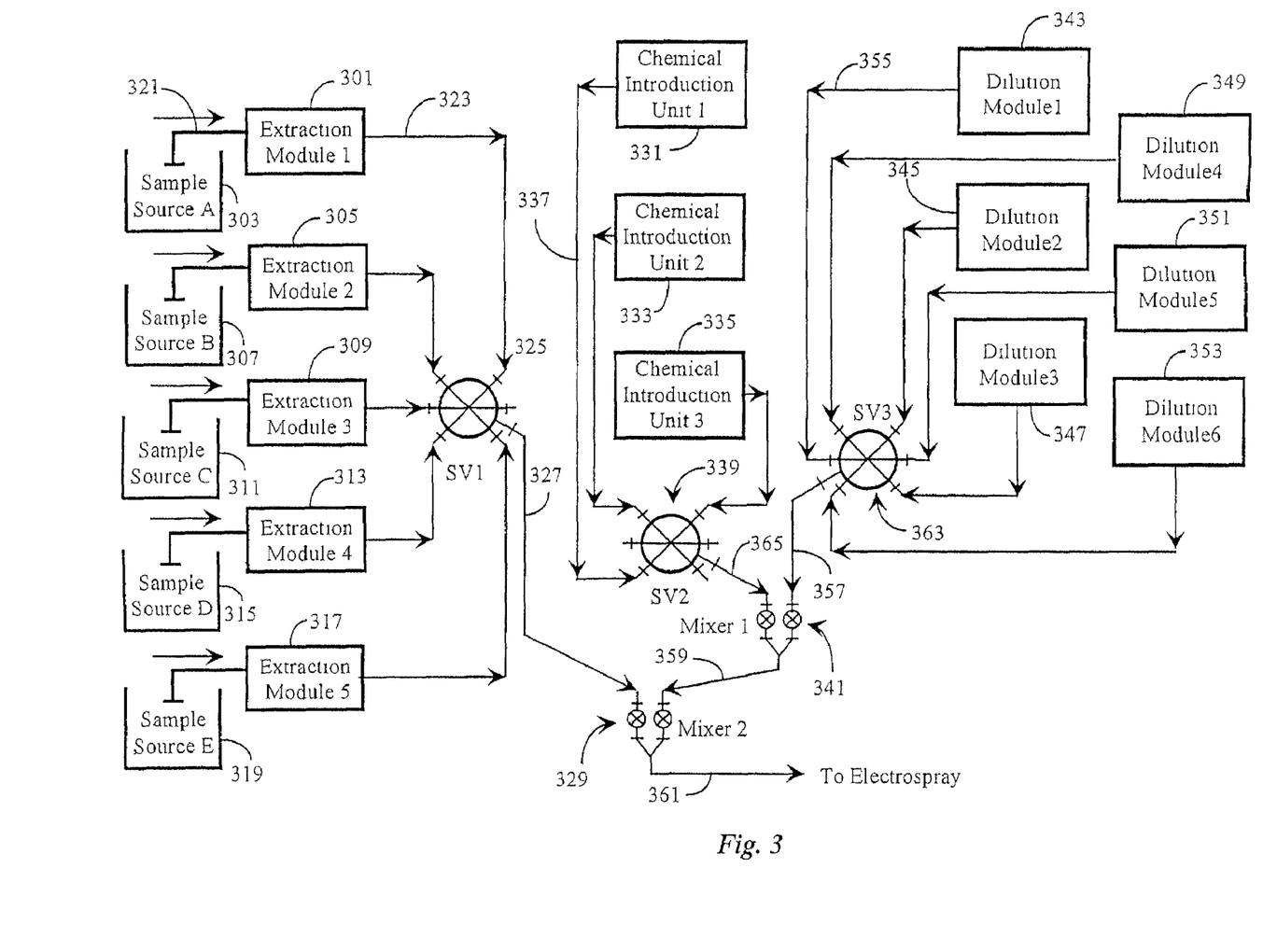
FIG. 3 is a block diagram illustrating in more detail a modular instrument after the abstract model of FIG. 2.

FIG. 3 is a block diagram illustrating in more detail a modular instrument after the abstract model of FIG. 2. In the modular unit of FIG. 3 there are illustrated five extraction modules, three chemical introduction modules, and six dilution modules, all interconnected by fluid conduits and switching valves to manage samples and ultimately deliver prepared samples to electrospray and hence to mass spectrometry. The chemical introduction modules and dilution modules are both dedicated to modifying samples or portions of samples extracted by the extraction modules.

More specifically extraction modules 301, 305, 309, 313, and 317 are shown paired with wet-baths 303, 307, 311, 315, and 319, respectively. Each extraction module is connected to its wet bath by at least one fluid conduit, as module 301 is shown connected to bath 303 by exemplary conduit 321.

In practice, the extraction modules are a part of an instrument in an embodiment of the present invention, and are implemented in a cabinetry somewhat remote necessarily from the baths to be monitored. Part of the reason is that the baths are spaced apart by the needs of manufacturing steps in the fab, and the instrument of the invention is not necessarily a welcome guest in the clean room. Exemplary conduit 321 for each bath and extraction module pair, then, will be of significant length. This fact necessitates a relatively high flow rate of sample from a bath, say bath 303, to a reservoir in an extraction unit, for example unit 301. A relatively high flow rate is needed to ensure adequate sample to maximize efficiency of the monitoring system, partly because the distances between points within the system between which sample solution must be passed, are very much shorter distances than the initial distance from the bath to the first reservoir in the system.

The extraction modules are unique sub-systems which, under management by the computer control system partly described above, draw raw sample quickly from baths to be monitored, on a timed basis, effectively separate drawn sample volumes from the bath, preventing any backflow or migration of sample, and the separation allows provision of a portion of the drawn sample at a completely different flow rate (lower), and in precise volume, to other elements of the system.

In each sample cycle each extraction module provides a precise raw sample portion of the original draw, in this embodiment, to a switching valve (SV), represented in FIG. 3 as SV1. The SVs are valve apparatus that allow a number of incoming conduit paths to be selectively switched to a single directed output. For example, a precise sample volume from extraction module 1 (301) through exemplary conduit 323 will be switched through SV1 (325) into conduit 327 to be delivered into an equalibrator (mixer) 329, labeled here as Mixer 2.

In each extraction cycle for each extraction module a sample volume is drawn from the bath associated with the extraction module. The volume drawn is regulated, but need not be controlled with the precision imposed in subsequent operations, because only a precisely-measured portion of the drawn sample will be sent on for analysis. It is known that sample constituency changes over time (which is the motivation for precision monitoring), so it is necessary to discard that portion of an originally-drawn sample that is not used, and also to flush, purge, and clean the extraction module for the next cycle, lest material remaining from a previous sample contaminate a new sample. Unique features of the extraction modules accomplish these necessities, and detail is provided below.

While one extraction module is delivering a precisely measured portion of an original sample to mixer 2 (329) all other extraction modules are isolated from the mixer. Also, to maximize efficiency, a maximum number of samples need be analyzed in a minimum time. Therefore, while one extraction module is delivering its sample, the others are in various other stages of their individual extraction cycles. The operations are precisely timed by the control system (not shown in FIG. 3) so, as soon as one module, 301 for example, finishes its delivery, another module is ready to deliver, and so on.

There is, following the above description of extraction cycles, a steady sequence of raw samples delivered to mixer 2 by the extraction modules in order, and each sample is a precisely measured portion of an original sample. Each sample to mixer 2, however, is not ready for injection into an analytical instrument. Some chemical treatment may be necessary, and introduction of spike solution is always necessary for the methods of the invention.

There are in the illustrated preferred embodiment six dilution modules, labeled Dilution Module 1 through Dilution Module 6, and each is connected via fluid conduit and appropriate check and pinch valves (not shown) and the like to a switching valve 3 (363), which is analogous to SV1 described above, in that it provides selective passage to one out line for several in lines. By controlling SV3 (363) one may introduce spike solution from any one of the dilution modules through SV3 into conduit 357, and hence into Mixer 1 (341).

Dilution modules 1–6 provide a range and variety of spiking solutions, each of which has an isotope constituency for an element to be measured in one of the known wet baths to be monitored, and the ratio of isotopes is known and differs substantially from the isotope ratio occurring naturally for a specie to be measured. Each of the dilution modules, in fact, is a sophisticated subsystem capable not just of selecting an isotope mix for introduction, but also of preparing isotope spikes of very low concentration on-the-fly for reasons that will be made clear in further description to follow.

There are three chemical introduction units labeled as units 1, 2, and 3, and labeled also element numbers 331, 333 and 335 respectively. These modules are for introducing chemicals for any of a range of purposes as described briefly above, such as to neutralize strong acid or base components of introduced samples. Each of these units is charged with appropriate chemicals for the kinds of baths to which the system will be devoted. Further, each is capable of introducing precisely measured quantities of these chemicals, under control of the computerized control system described briefly above. These chemical constituents are provided on demand to switching valve SV2, and thence to mixer 1 (341) via conduit 365.

As previously described, selected spikes from dilution modules 1 through 6 are also provided to mixer 341, which mixes the appropriate spike with appropriate chemical (if needed), and the resultant mixture goes to mixer 2 via conduit 359. Timing and control is such that all of the appropriate constituents, being the precisely measured sample, the appropriate treatment chemicals, and the isotope spike, meet in mixer 2 and are eqalibrated there. The mixed result is conducted via conduit 361 to an electrospray ionization unit (atmospheric ion generator 211) from FIG. 2. The treated and spiked sample, vaporized and ionized, now goes to the mass spectrometer, and the ratio of isotopes found by the mass spectrometer may be used to determine the concentration of the specie sought for the bath monitored.

It will be apparent to the skilled artisan that the number and arrangement of modules may differ in different embodiments, and may be determined, at least in part, by the nature of the systems to be monitored and analyzed. Also, the chemicals and spikes with which modules will be charged will be largely determined by the application and nature of system to be analyzed. Further, although FIG. 3 shows chemicals mixed with spike before mixing with sample, another order may be used in some embodiments.

Extraction Modules

Figure 4:
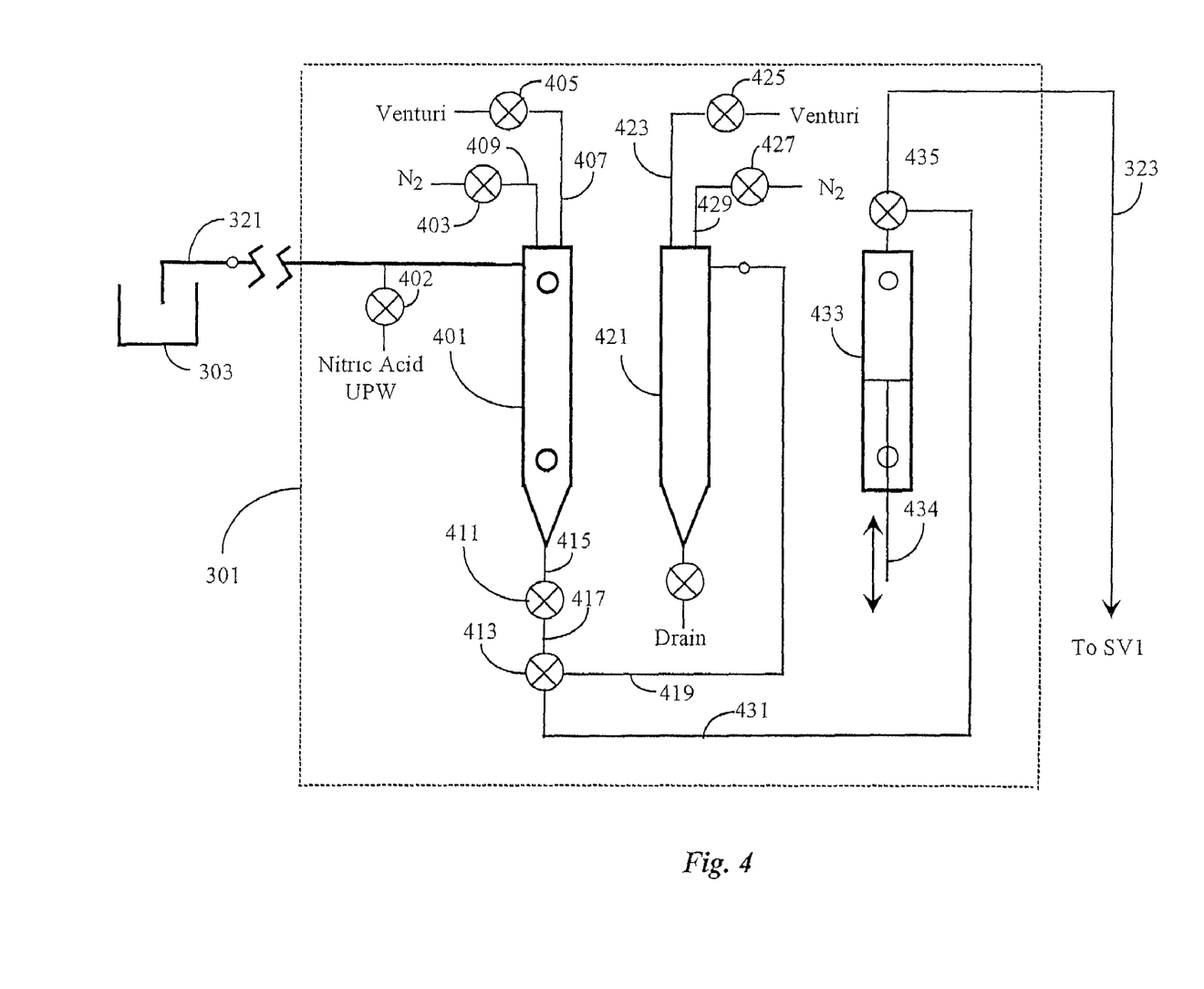
FIG. 4 is a schematic diagram illustrating an extraction module from FIG. 3 in expanded detail.

FIG. 4 is a somewhat more detailed illustration of one of the five extraction modules from FIG. 3. For illustration purposes the module shown is module 301, as indicated, connected to bath 303 by conduit 321. A primary component of the extraction module is a mini-reservoir 401 for collecting an original sample from bath 303. Mini-reservoir 401 is connected by a conduit 409 to a pressure-controlled nitrogen source through a pinch valve 403, and by a second conduit 407 through a pinch valve 405 to a venturi vacuum source To draw a sample from bath 303, which, as described previously may be at a considerable distance from the extraction module, valve 405 is opened with valve 411 held closed, which creates a vacuum in the mini-reservoir and causes fluid to be drawn from bath 303. In some cases valve 403 may also be opened allowing nitrogen to flow into the mini-reservoir, and the pressure on the nitrogen source is controlled to help control the vacuum in the reservoir, while also providing a protective cover of nitrogen. This is a timed operation under control of the computer-control system, operating through an input/output (I/O) interface which controls diaphragms, for example, in valves 403 and 405. In this example liquid is quickly drawn into reservoir 401 in a time short enough that the overall cycle of the system will not be impeded.

When enough liquid is in reservoir 401, valves 403 and 405 are closed, stopping the liquid draw, and leaving a protective nitrogen blanket over the sample. The next operation is to draw a precise-volume sample from reservoir 401 into a syringe 433. This is done by opening valve 411, switching valve 413 to provide an exclusive path from conduit 415 to conduit 431, switching valve 435 to provide an exclusive path from conduit 431 into the syringe, and withdrawing plunger 434 by a precise distance to draw in the precise volume of the raw sample. Plunger 434 is operated in a preferred embodiment by the computerized control through a precision electric motor, such as a stepper motor, and a threaded mechanism, providing precise distance and time control for the plunger, and allowing the rate at which the plunger is withdrawn or extended to be varied in a highly accurate manner.

When the precise volume of sample is drawn, valve 413 is operated to close the path from conduit 417 to conduit 431. Now the precision sample is isolated in syringe 433, and ready to be injected through valve SV1 (325) into mixer 329. This injection operation is programmed to occur at the proper time in concert with injection from a dilution module, and possibly a chemical introduction module, through mixer 1 to mixer 2. Also, the rate of injection may be precisely controlled by the management and control system through whatever translation device drives the plunger of the syringe.

After a precision sample is in place for injection, reservoir 401 and connecting conduit and the like may be purged and prepared for a next sample. This done by opening valve 402 to introduce one or both of nitric acid and ultra-pure water (UPW), while opening valve 425 to provide vacuum to drain reservoir 421. Valve 413 has already been shifted after the draw of precision-volume sample to provide a path from conduit 417 to conduit 419. Nitrogen may again be used by opening valve 427 to reservoir 421 through conduit 429. In this operation the remaining contents of reservoir 401 are drawn into reservoir 421 along with one or both of UPW and nitric acid, leaving reservoir 401 flushed, cleaned, and empty except for a protective nitrogen atmosphere.

At this time reservoir 401 is ready for another extraction cycle, and may proceed to draw another raw sample from the associated bath, although this will typically be delayed according to a predetermined schedule. Once all refuse material is in reservoir 421, valve 420 is opened with valve 425 closed and valve 427 open, and nitrogen pressure urges all the refuse to drain. During this time the precision sample in syringe 433 may have been injected into mixer 2 via SV1, or may still be waiting for the proper time to do so.

Chemical Introduction Modules

Figure 5:
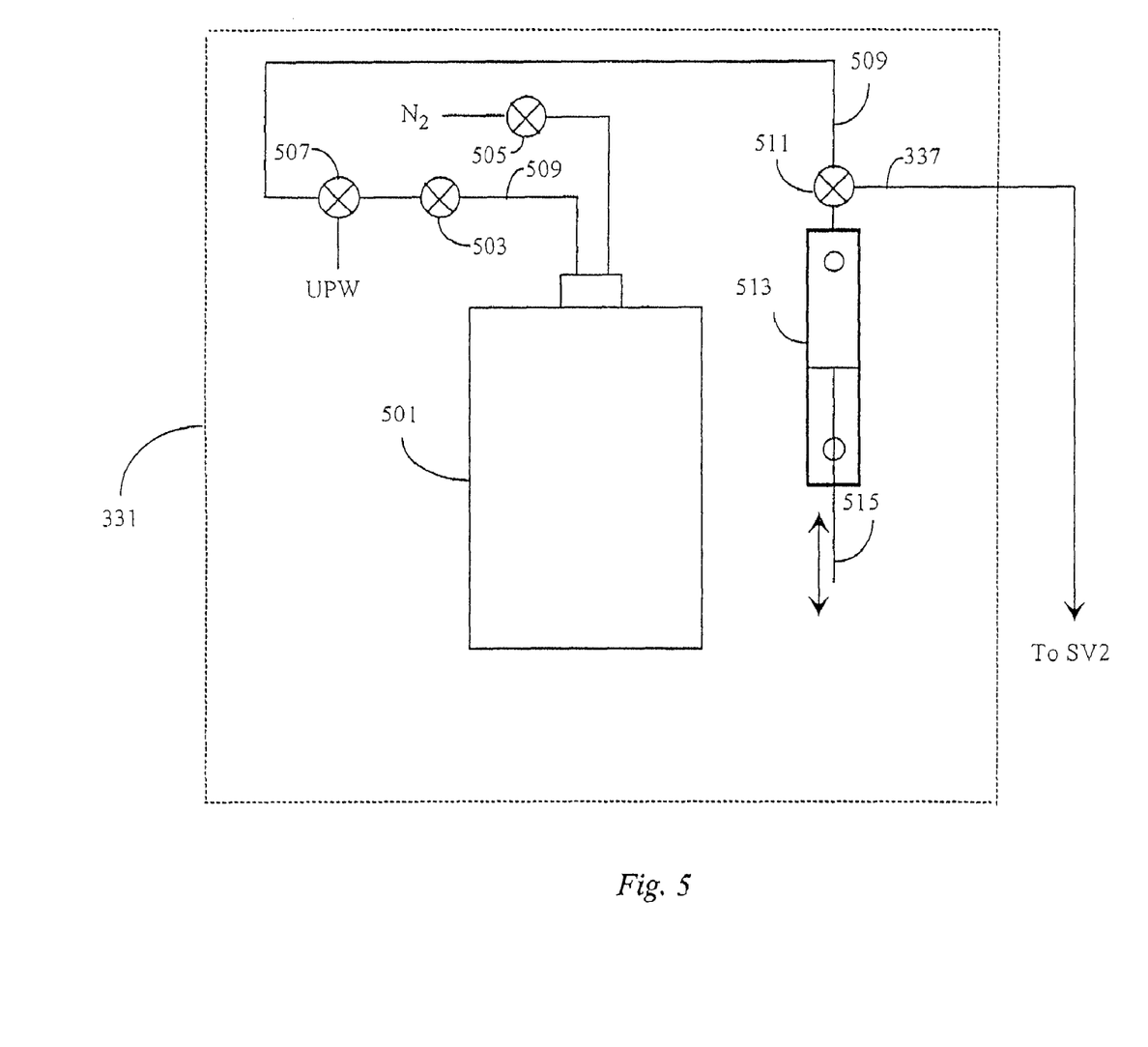
FIG. 5 is a schematic diagram illustrating a chemical introduction unit from FIG. 3 in expanded detail.

FIG. 5 is a schematic diagram illustrating a chemical introduction unit from FIG. 3 in expanded detail. In this description, module 331 from FIG. 3 is shown. Module 331 has a chemical reservoir 501 containing the appropriate chemical. A syringe 513 is connected to reservoir 501 via conduit path 509 through a three-way valve 511, a second three-way valve 507, and a pinch valve 503. A pressure-controlled nitrogen source is connected through a pinch valve 505.

In operation, plunger 515 is withdrawn with valve 511 connecting the syringe to path 509 through valve 507 switched to provide the proper path and open valve 503. A precise volume of the chemical solution is drawn into the syringe, and may then be injected at the appropriate time and at an appropriate rate by switching valve 511 to provide a path between the syringe and conduit 337 (see FIG. 3), which conducts the chemical introduced to SV2 and then mixer 1. A source of UPW (ultra pure water) is also made available through three-way valve 507, and nitrogen through valve 505. During syringe loading valve 505 is opened to prevent a vacuum being drawn on the reservoir by the syringe action.

Dilution Modules

Figure 6:
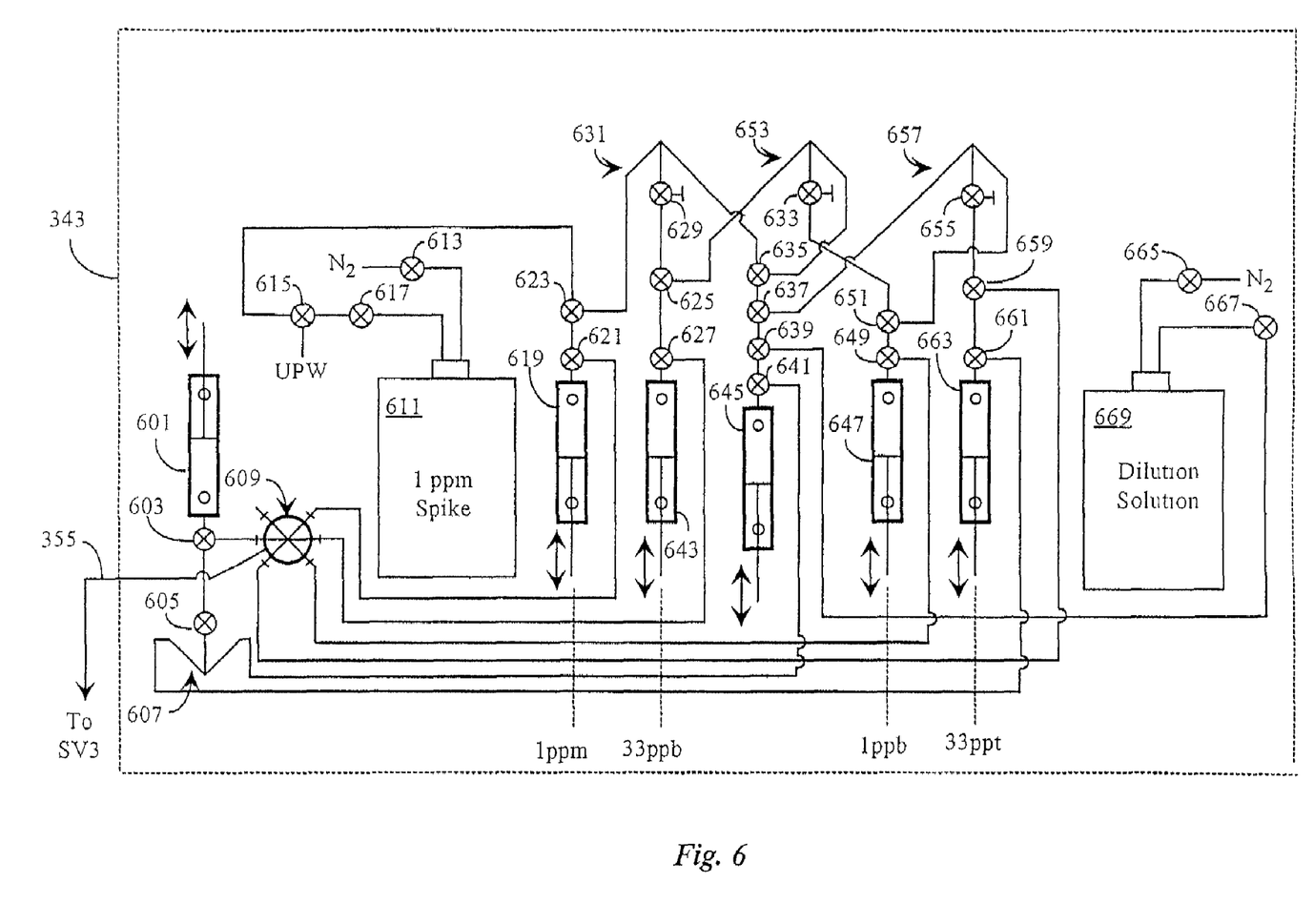
FIG. 6 is a schematic diagram illustrating a dilution module unit from FIG. 3 in expanded detail.

FIG. 6 is a schematic diagram illustrating a dilution module unit from FIG. 3 in expanded detail. A primary purpose of a dilution module in embodiments of the present invention is to provide spike solution in any of several very dilute concentrations. It is necessary in embodiments of the invention that the relative concentration of the spike for any specie for which monitoring is accomplished be in the same general range as the expected concentration in the sample. If the spike concentration is either much to high or much too low, then the mass spectrometer will not be able to provide a ratio of isotopes with adequate resolution to determine the sample concentration. Further, it is known to the inventors that spike solution in most cases remains stable in concentration down to about 1 ppm. Much below that value the spike concentration cannot stay constant for a number of reasons. For example, there are boundary layer effects that are involved in solution stability. At and above about 1 ppm isotopes tend to reach an equilibrium in adhering to and escaping from walls of a reservoir. Below that concentration the concentration will fall as more isotopes precipitate from solution at walls of the reservoir, and are not replaced. There are other effects as well that render lower concentrations unstable.

Because of these effects the present inventors have provided a dilution module that stores a stable solution of isotopes at a not-naturally-occurring ratio, in this case at 1 ppm, and prepares lower concentrations as needed by precision dilution and mixing. Referring now to FIG. 6, a reservoir 611 stores a relatively large volume of spike solution at 1 ppm. By a relatively large volume is meant enough to allow the instrument to operate for a considerable period of time, such as several days, without requiring replenishment. A primary syringe 601 is provided, connected to the 1 ppm reservoir 611 through conduits and valves, and also to an arrangement of secondary syringes 619, 643, 645, 647 and 653, and to mixers 607, 631, 653 and 657 through other conduits and valves, and all of these elements are interconnected in a manner that allows for sequential and precision dilution of the 1 ppm solution in steps from 1 ppm, to 33 ppb, to 1 ppb, to 33 ppt, and finally to 1 ppt. The steps in this example, and the arrangement of elements to accomplish same, are exemplary, and the skilled artisan will recognize that there are many other arrangements and steps that might be accomplished completely within the spirit and scope of the invention.

Communication between primary syringe 601 and the arrangement of secondary syringes and other elements is through a switching valve 609. In the event 1 ppm spike is needed, for example, syringe 619 is used through valves 621 and 623 to draw a precise amount from reservoir 611, and the 1ppm volume is then transferred to syringe 601 by switching valve 621 to the right-hand position, and switching valve 609 to transfer the volume through valve 603 and into syringe 601. When the spike is needed for a sample to be analyzed, switching valve 609 is positioned with valve 603 open to syringe 601 to allow syringe 601, by driving its plunger, to move the spike into conduit 355 and on to SV3 (see FIG. 3).

The arrangement and sizing of syringes, as well as the distance of driving plungers and the rate of plunger travel, is such that a 1 ppm spike may be mixed with a syringe of dilution solution to accomplish a syringe of 33 ppb, and a 33 ppb spike in a syringe may be mixed again with a syringe of dilution solution to accomplish a 1 ppb solution, and so on. A description of every operation in all instances would be highly redundant, so only a smaller description is given here.

Assume that a 33 ppb spike is required. The first step is the same as for the 1 ppm spike as described above, that is, 1 ppm spike is drawn from reservoir 611 into syringe 619. During this operation valve 613 may be opened to a controlled-pressure nitrogen source for the same purposes as previously described. While the 1 ppm solution is drawn into syringe 619, valves 641, 639, and 667 are set to connect syringe 645 to reservoir 669, and a precise volume of dilution solution is drawn into syringe 645. Now valve 667 is closed, and valves 641, 639, 637, and 635 are reset to straight-through, connecting syringe 645 to mixer 631 through an input conduit. At the same time, after syringe 619 is filled with the 1 ppm solution, valves 621 and 623 reset to connect syringe 619 to mixer 631 through another input conduit. The arrangement of the input conduits are such that substantial fluid direction change will occur as syringes 619 and 645 are operated in concert, thereby aiding mixing. Syringes 619 and 645 are now operated in concert with syringe 643 with valves 625 and 627 set straight-through, and the volume of 1 ppm solution from syringe 619 is mixed with the dilution solution in syringe 645 through mixer 631 and into syringe 643. At the end of this operation accomplished through valve manipulation and manipulation of the appropriate syringe plungers, syringe 643 has a precise spike at 33 ppb.

From this point valves 627, 609, and 603, along with the plungers of syringes 601 and 645 are operated to transfer the 33 ppb spike into syringe 601, where it will be ready for transfer, as described above, again through valve 609 into conduit 355 and on to SV3 (see FIG. 3).

Given the arrangement of the elements labeled in odd numbers from 601 through 669 in FIG. 6, given the description above and the teaching of the invention provided herein, the skilled artisan can easily understand operation of the elements to accomplish the further dilutions to six orders of magnitude below 1 ppm. There are, in fact, a variety of options in the ways that elements may be controlled to accomplish dilutions, and the apparatus illustrated and described in FIG. 6, given different starting concentration, and different programming in different embodiments is capable of providing near-real-time dilutions from any reasonable starting concentration with any reasonable species and solvents, to many other lesser concentrations. In many cases as well, there may be more than a single specie with unnatural isotope ratios in individual ones or each of the several dilution modules shown in FIG. 3, and described with the aid of FIG. 6.

Control System

Figure 7:
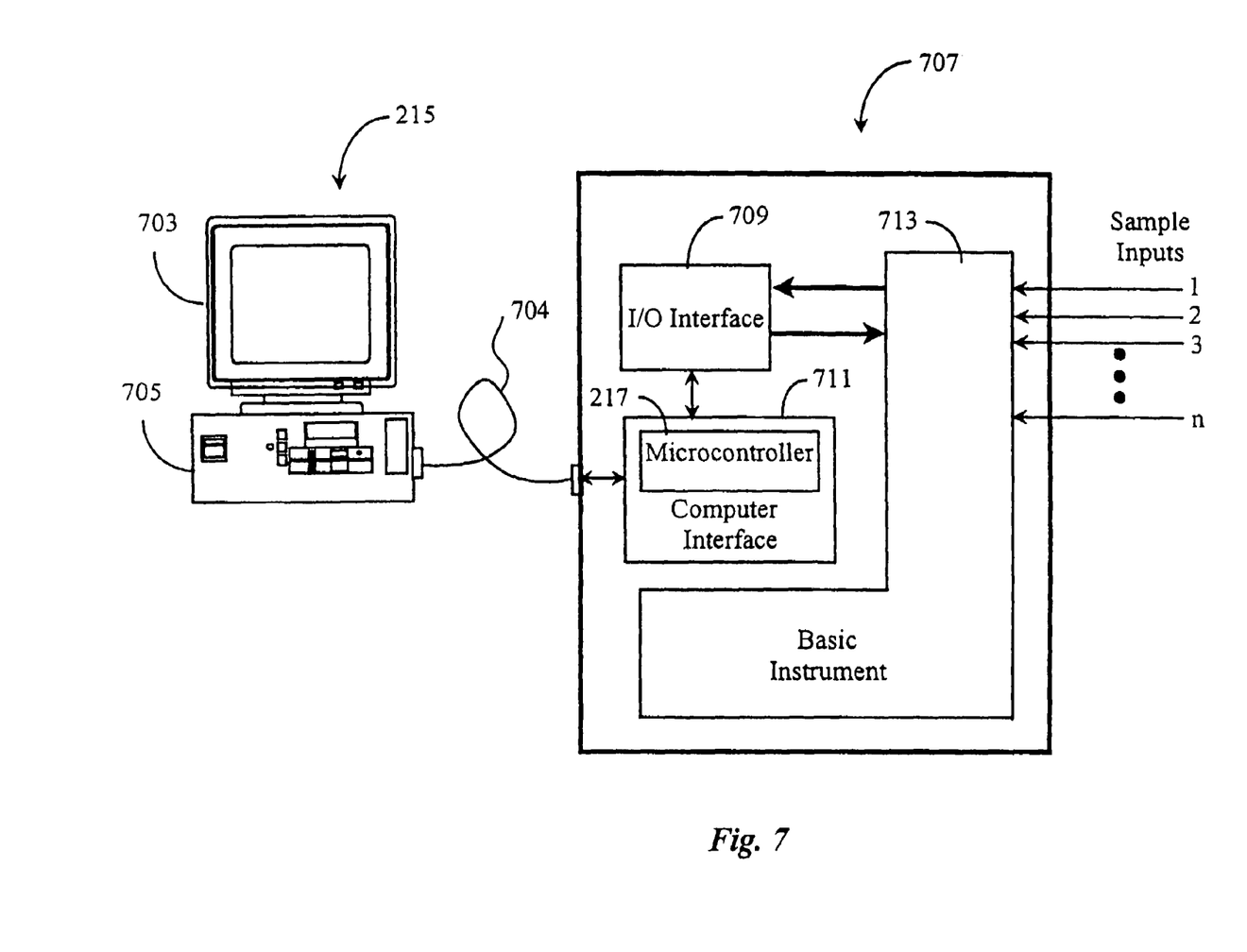
FIG. 7 is a block diagram of a control system used in an embodiment of the present invention.

FIG. 7 is a block diagram of a control system for an instrument in an embodiment of the present invention. Instrument 707 in FIG. 7 represents an instrument as shown abstractly in FIG. 2. With the exception of a computer station 215, comprising a computer 705 and a display unit 703, all of the components of the instrument are housed in a common cabinet, which may be positioned in a convenient location to fluid systems to be monitored, such as in a maintenance area outside the strict clean-room environment in a semiconductor fab. Computer 215 is analogous to the element with the same number in FIG. 2, and can be such as a high-end PC. Computer 215 is connected by a communication link 704 to the instrument 707, and this link can be any of several types, such as a serial link or a parallel communication link. Other links are also possible.

Computer station 215 is connected within the instrument cabinet to a computer interface 711, which comprises a microcontroller 217, which is analogous to controller 217 in FIG. 2. Microcontroller 217 comprises firmware, some of which is in standard form (proprietary), and some of which may be pre-programmed for a specific application. For example, in a semiconductor clean room application, firmware may be provided to cycle elements of the instrument in a manner dictated by and compatible with certain specific fluid systems to be monitored.

Microprocessor 217 is connected to an I/O interface 709 for controlling the fluid-handling and other elements of the instrument. It is well-known in the art that drive motors as used for such as syringe plungers, solenoids to drive diaphragms for pinch valves, multi-path switching valves, and the like, are all driven by AC or DC signals providing the voltage and current necessary to drive the specific elements. The I/O interface accepts computer-level signals from microprocessor 217 for manipulating elements of the instrument, and provides the correct signals as needed for each element in the voltage, current, and time required. There are also in many instances signals delivered back to I/O interface 709 from sensors in the instrument, such as position sensors on syringe plungers, which are translated to appropriate computer voltage and provide to microcontroller 217.

FIG. 3 also illustrates sample inputs 1-n, which are analogous to conduits 321 of FIG. 3, delivering samples from monitored fluid systems to the instrument. In operation, the samples come in, chemical corrections are made, spikes are added, samples are vaporized and ionized, and analyzed by the mass spectrometer, all within portion 713 within instrument 707. Data and information derived is transmitted to computer station 215, and may be further manipulated, then displayed on monitor 703 for elucidation of maintenance personnel. In other cases data may be integrated with other control code and archived for historical purposes, and also used in other automated control functions. There are many possibilities. Computer station 215 operates executing a program suite proprietary to the instrument described herein, and is the subject of one or more separate patent applications.

Description Summary

A general instrument has been described above for monitoring, and in some cases triggering maintenance of concentration of species in fluid systems, and also for monitoring contamination of the systems. In specific embodiments, the instrument has been described as an instrument applied to monitoring wet-baths in semiconductor manufacturing. The invention, however, has considerably broader application, and may be configured for a broad variety of other purposes without departing from the spirit and scope of the invention. For example, such an instrument has broad application in such as trace element contamination of well water and ground water in environmental studies, and in many other environmental applications.

The instrument as described in embodiments herein is broadly applicable to analytical techniques that may vary in considerable detail form the exemplary applications discussed thus far. For example, in some cases addition of standard concentrations of monoisotopic elements, that is, elements that do not exhibit a plurality of isotopes in the natural state, may be used in many procedures, for example to validate estimates. Further, in many alterations of the invention the analytical technique may be other than mass spectroscopy, such as non-mass spectroscopy (for example optical spectroscopy), and chromatography.

In another embodiment a verification technique may be used incorporating addition of a known amount of an element to a sample to see if the signal increase is proportional and quantifiable with the amount added.

Further, although the instrument has been described having a specific number of inputs and a specific number of dilution modules and the like, these numbers can be altered considerably without departing from the spirit and scope of the invention. The nature of the modules may also be altered in alternative embodiments, and there are a broad variety of such changes that could be made. Accordingly the invention must be accorded the scope of the claims below.

What is claimed is:

1. An in-process ratio mass spectrometry system, comprising:
   a sample extraction module adapted to extract a predetermined volume of sample from a process bath;
   a spike reservoir;
   a spike dilution apparatus coupled to the spike reservoir and configurable to dilute a spike from the spike reservoir having a first concentration to produce a known volume of processed spike having a diluted second concentration;
   a mixer coupled to the spike dilution apparatus and the sample extraction module, the mixer being configurable to mix the known volume of processed spike and known volume of extracted sample having at least one analyte to permit equilibration therebetween;
   an atmospheric pressure ionizer (API) coupled to the mixer and configurable to ionize the equilibrated extracted sample and processed spike to produce ions;
   a mass spectrometer coupled to the API and configurable to process the ions by ratio determination; and
   a control system adapted to automatically configure the sample extraction module, the spike dilution apparatus, the mixer, the API, and the mass spectrometer such that the sample is automatically extracted, mixed with the processed spike, ionized, and processed by to mass spectrometer, the control system being further configured to use the ratio measured by the mass spectrometer to characterize the concentration of the at least one analyte in the extracted sample.

2. The system of claim 1, wherein the at least one process solution comprises a plurality of process solutions, the sample extraction apparatus being further configured to extract the sample from a process solution selected from the plurality of process solutions as controlled by the control system.

3. The system of claim 1, wherein the spike dilution apparatus includes a plurality of dilution sub-modules arranged from first dilution sub-module to a last dilution sub-module, wherein each dilution sub-module is configurable to achieve a dilution selected from a range of possible dilutions, wherein the first dilution sub-module is configurable to dilute the spike having the first concentration to a first diluted concentration, the second dilution sub-module is configurable to dilute the spike at the first diluted concentration to a second diluted concentration, and so on such that the last dilution sub-module is configurable to provide the spike diluted to a last diluted concentration, and wherein the control system is operable to configure the appropriate combination of dilution sub-modules to produce the known volume of processed spike having the second concentration.

* * * * *